United States Patent
Wolff et al.

(10) Patent No.: US 8,304,375 B1
(45) Date of Patent: Nov. 6, 2012

(54) FOAMING FORMULATIONS INCLUDING SILICONE POLYESTERS

(75) Inventors: Kelly Laura Wolff, Appleton, WI (US); Corey T. Cunningham, Larsen, WI (US); Jeffery Richard Seidling, Appleton, WI (US); Thomas O'Lenick, Dacula, GA (US); Anthony O'Lenick, Dacula, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/460,300

(22) Filed: Apr. 30, 2012

Related U.S. Application Data

(60) Provisional application No. 61/627,478, filed on Oct. 13, 2011.

(51) Int. Cl.
*C11D 9/36* (2006.01)
*C11D 3/43* (2006.01)

(52) U.S. Cl. ........ 510/138; 510/119; 510/122; 510/130; 510/135; 510/137; 510/466

(58) Field of Classification Search ............... 510/119, 510/122, 130, 135, 137, 138, 157, 466
See application file for complete search history.

(56) References Cited

U.S. PATENT DOCUMENTS

| | | | |
|---|---|---|---|
| 3,849,241 A | 11/1974 | Butin et al. |
| 4,100,324 A | 7/1978 | Anderson et al. |
| 4,440,653 A | 4/1984 | Briscoe et al. |
| 5,284,703 A | 2/1994 | Everhart et al. |
| 5,350,624 A | 9/1994 | Georger et al. |
| 5,629,006 A | 5/1997 | Hoang et al. |
| 5,635,462 A | 6/1997 | Fendler et al. |
| 5,843,881 A | 12/1998 | Dubois et al. |
| 5,951,993 A | 9/1999 | Scholz et al. |
| 6,117,440 A | 9/2000 | Suh et al. |
| 6,120,753 A | 9/2000 | Vinski et al. |
| 6,228,385 B1 | 5/2001 | Shick |
| 6,258,348 B1 | 7/2001 | Tsivkin |
| 6,315,991 B1 | 11/2001 | Zofchak et al. |
| 6,335,000 B1 | 1/2002 | Pratley |
| 6,432,393 B1 | 8/2002 | Bergmann et al. |
| 6,723,310 B2 | 4/2004 | Zofchak et al. |
| 6,946,413 B2 | 9/2005 | Lange et al. |
| 6,949,249 B2 | 9/2005 | Healy et al. |
| 7,202,209 B2 | 4/2007 | Chang et al. |
| 7,381,417 B2 | 6/2008 | Gamez-Garcia |
| 7,651,990 B2 | 1/2010 | Asmus |
| 7,670,615 B2 | 3/2010 | Veeger et al. |
| 7,670,967 B2 | 3/2010 | Runge et al. |
| 7,842,725 B2 | 11/2010 | Wegner et al. |
| 7,892,643 B2 | 2/2011 | Kutsovsky |
| 7,893,285 B2 | 2/2011 | Bettle, III |
| 2002/0031486 A1 | 3/2002 | Lunsmann et al. |
| 2005/0265936 A1 | 12/2005 | Knopf et al. |
| 2006/0204466 A1 | 9/2006 | Littau et al. |
| 2006/0281663 A1 | 12/2006 | Asmus |
| 2007/0184016 A1 | 8/2007 | Macinga et al. |
| 2008/0215020 A1 | 9/2008 | Reeves et al. |
| 2009/0018047 A1 | 1/2009 | Mundschau et al. |
| 2009/0018213 A1 | 1/2009 | Snyder et al. |
| 2009/0214628 A1 | 8/2009 | de Rijk |
| 2009/0258812 A1 | 10/2009 | Sengupta et al. |
| 2009/0325837 A1* | 12/2009 | Mundschau et al. .......... 510/139 |
| 2010/0021464 A1 | 1/2010 | Archambeau et al. |
| 2010/0317595 A1 | 12/2010 | Mullins et al. |

FOREIGN PATENT DOCUMENTS

| | | | |
|---|---|---|---|
| AU | 2006222502 B2 | 9/2006 |
| EP | 1552807 A1 | 7/2005 |
| EP | 1811013 B1 | 8/2009 |
| EP | 2242475 B1 | 7/2011 |
| WO | 0032575 A1 | 6/2000 |

* cited by examiner

*Primary Examiner* — Charles Boyer
(74) *Attorney, Agent, or Firm* — Armstrong Teasdale LLP

(57) ABSTRACT

Foaming formulations including silicone polyesters are disclosed. These foaming formulations are useful as cleansing formulations such as used in hand sanitizers. The foaming formulations provide improved aesthetic properties and foaming appearance, while maintaining high antimicrobial capacity.

20 Claims, No Drawings

FOAMING FORMULATIONS INCLUDING SILICONE POLYESTERS

This application claims priority from U.S. Provisional Application Ser. No. 61/627,478 filed on Oct. 10, 2011, which is hereby incorporated by reference in its entirety.

BACKGROUND OF THE DISCLOSURE

The present disclosure relates generally to a formulation comprising a silicone polyester. The silicone polyester provides the formulation with an improved foaming property. The foaming formulations of the present disclosure are useful as cleansing formulations such as used in alcohol-based hand sanitizers.

According to the Center for Disease Control, proper cleansing can be one of the most effective steps taken to prevent the spread of diseases and infections. Specifically, proper bodily cleansing according to various sources requires not only using soap but also washing for a sufficiently long period of time in order to remove dirt and any microorganisms that may be present on the skin. For example, the Center for Disease Control has stated that effective cleansing should last at least 15 seconds.

As many consumers fail to effectively cleanse using soaps, alcohol-based sanitizing solutions capable of providing effective antimicrobial sanitation for hand or body cleansing purposes have been developed. Various forms of alcohol-based antimicrobial compositions are known in the art and have been used in the healthcare industry, food service industry, and private sector by individual consumers to provide a convenient means to control and prevent the spread of potentially harmful bacteria and other microorganisms. The alcohol-based antimicrobial compositions are typically utilized to cleanse the skin by destroying bacteria and other microorganisms present thereon, especially on the hands, arms, and face of the user.

In addition to the effective sanitizing, the use of alcohol-based antimicrobial compositions typically does not require subsequent drying of the skin, such as by means of wiping involved in the cleaning process using soap and water. That is, the relatively high alcohol content (e.g., greater than 60% by weight) in the compositions allows for fast and essentially complete evaporation of the liquid components of the composition from the skin.

Conventionally, these alcohol-based antimicrobial compositions further include viscosity increasing agents to prevent runoff and to increase residence time on the skin. Such products are known as alcohol gels. While longer residence time tends to enhance antimicrobial action, it also tends to magnify certain undesirable side effects. In particular, frequent use of alcohol gels may cause skin irritation and dryness. This can be a problem for health care professionals, child care providers, food service workers and others who use alcohol gels to disinfect or sanitize their hands multiple times in a day.

To counteract the drying and irritating effects of alcohol gels, foaming alcohol formulations including conventional ethoxylated silicones or conventional fluorinated compounds have been developed. However, these agents used to create the foam in the alcohol formulations may cause the formulations to have poor aesthetics and/or skin feel properties, as well as poor foam stability. In addition, conventional fluorinated compounds impose potential environmental and safety concerns.

Accordingly, there is a need for a foaming formulation that provides effective skin cleansing and sanitizing effects, while having good foam stability. It would further be advantageous if the foaming formulations provided improved aesthetic properties and foaming appearance, while maintaining high antimicrobial capacity.

BRIEF DESCRIPTION OF THE DISCLOSURE

It has now been unexpectedly found that cleansing foaming formulations can be formed without the use of conventional ethoxylated silicones and conventional fluorinated compounds. Particularly, the foaming formulations of the present disclosure include silicone polyesters that are surprisingly highly efficient foaming agents for hydro-alcoholic solutions. Specifically, the silicone polyesters surprisingly provide outstanding foam when used in hydro-alcoholic solutions having high alcohol content (e.g., greater than 50%, and typically above 70%, by weight of alcohol).

The foam of a foaming formulation is a two phase system comprised of gas cells, or bubbles, that are surrounded by a thin, continuous liquid film phase. The amount of liquid in the thin film defines the type of foam that is generated. For example, conventional detergent solutions and foaming alcohol sanitizer formulations are classified as "wet foams". In a wet foam, the liquid is mainly found in the junctions between gas bubbles, known as "Plateau borders". As the amount of liquid increases relative to the amount of gas bubbles, the thin liquid films surrounding the bubbles and the Plateau borders swell, forcing the bubbles to take a spherical shape. As the swelling increases, the borders lose rigidity and fall apart, causing the foam to degrade into a bubbly liquid that has no overall order or rigidity.

In completely aqueous foams, conventional foaming agents (e.g., conventional ethoxylated silicones and fluorinated compounds) are concentrated at the surfaces of the gas bubbles. This organization stabilizes the thin liquid films against rupture. In hydro-alcoholic foaming formulations, such as foaming alcohol sanitizing formulations, however, the presence of the alcohol affects the organization of the conventional foaming agents and the rate of evaporation of the formulation becomes a significant variable. It is believed that these two factors neutralize the ability of conventional foaming agents to create and stabilize foam.

It has now been unexpectedly discovered that specific amphiphilic terpolymers can overcome the stability problems to generate a high quality, stable foam in hydro-alcoholic solutions. Further, it has been discovered that the polymeric nature of the foaming formulations of the present disclosure provide enhanced skin aesthetics (e.g., substantivity while formulation is in use, reduced tackiness during and after formulation use, soft and conditioned skin feel of formulation, and improved foam appearance).

Accordingly, the present disclosure is directed to a foaming formulation including water, an alcohol, and a silicone polyester. The silicone polyester has the following structure:

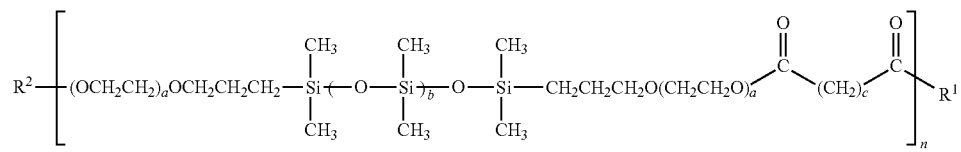

wherein R$^1$ is —O(CH$_2$CH$_2$O)$_x$CH$_3$; R$^2$ is —C(O)(CH$_2$)$_c$C(O)O(CH$_2$CH$_2$O)$_x$CH$_3$; a is an integer ranging from to 20; b is an integer ranging from 10 to 30; c is an integer ranging from 1 to 10; n is an integer ranging from 5 to 15; and x is an integer ranging from 5 to 25.

The present disclosure is further directed to a process of preparing a foaming formulation. The process includes mixing water, an alcohol, and a silicone polyester. The silicone polyester has the following structure:

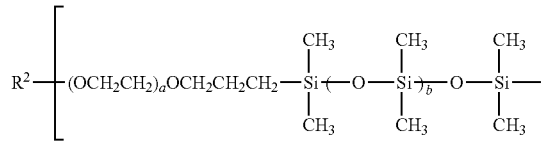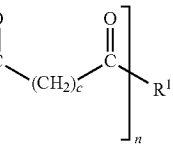

wherein R$^1$ is —O(CH$_2$CH$_2$O)$_x$CH$_3$; R$^2$ is —C(O)(CH$_2$)$_c$C(O)O(CH$_2$CH$_2$O)$_x$CH$_3$; a is an integer ranging from 5 to 20; b is an integer ranging from 10 to 30; c is an integer ranging from 1 to 10; n is an integer ranging from 5 to 15; and x is an integer ranging from 5 to 25.

The present disclosure is further directed to a method for bodily cleansing including topically applying to skin a foaming formulation. The formulation includes water, an alcohol, and a silicone polyester. The silicone polyester has the following structure:

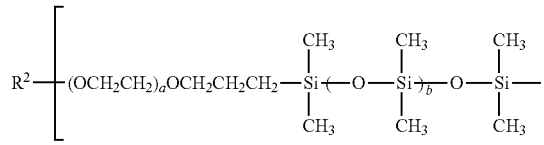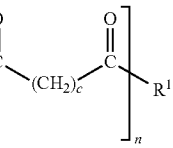

wherein R$^1$ is —O(CH$_2$CH$_2$O)$_x$CH$_3$; R$^2$ is —C(O)(CH$_2$)$_c$C(O)O(CH$_2$CH$_2$O)$_x$CH$_3$; a is an integer ranging from 5 to 20; b is an integer ranging from 10 to 30; c is an integer ranging from 1 to 10; n is an integer ranging from 5 to 15; and x is an integer ranging from 5 to 25.

Other objects and features will be in part apparent and in part pointed out hereinafter.

DETAILED DESCRIPTION OF THE DISCLOSURE

The present disclosure is directed to a foaming formulation comprising water, an alcohol, and a silicone polyester. The foaming formulation provides an improved foaming effect providing effective cleansing and sanitization of the body of a user, while further providing improved aesthetics and skin-feel. Surprisingly, the formulation has improved foam stability as compared to foaming formulations including conventional ethoxylated silicones and conventional fluorinated compounds.

Typically, the foaming formulations of the present disclosure include from about 5% by weight to about 45% by weight water, including from about 10% by weight to about 40% by weight, and including from about 20% by weight to about 30% by weight.

Additionally, the foaming formulations include an alcohol. Any C$_1$-C$_6$ alcohol typically used in the formulation art for providing antimicrobial activity, thereby killing and/or inhibiting the growth of bacteria and other microorganisms, can suitably be used in the formulations of the present disclosure. Particularly suitable alcohols include methanol, ethanol, n-propanol, isopropanol, n-butanol, tert-butanol, 2-butanol, pentanol, hexanol, or combinations thereof.

Typically, alcohol is present in the foaming formulations in an amount of at least 50% by weight, including from 50% by weight to about 90% by weight, including from about 60% by weight to about 80% by weight, and including from about 65% by weight to about 75% by weight.

In addition to the water and alcohol, the hydro-alcoholic foaming formulations of the present disclosure include a silicone polyester. The silicone polyester includes three active groups (i.e., an amphiphilic terpolymer) having differing solubilities in the hydro-alcoholic solution. These different solubilities allow for the enhanced stabilization of foam in the formulation. Further, the polymeric nature provides enhanced skin aesthetics and skin feel.

The silicone polyesters used in the formulations of the present disclosure are prepared by an esterification reaction, in which linear dicarboxylic acid reacts with poly(ethylene glycol) monomethyl ether and dimethicone copolyols (LDMC). The resulting silicone polyesters conform to the following structure:

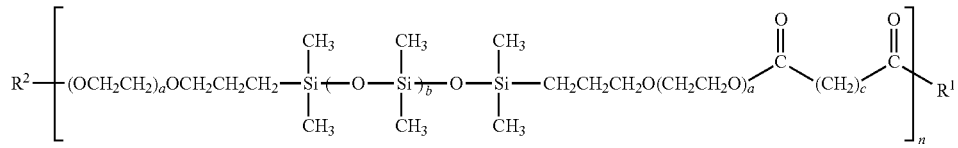

wherein R$^1$ is —O(CH$_2$CH$_2$O)$_x$CH$_3$; R$^2$ is —C(O)(CH$_2$)$_c$C(O)O(CH$_2$CH$_2$O)$_x$CH$_3$; a is an integer ranging from 5 to 20; b is an integer ranging from 10 to 30; c is an integer ranging from 1 to 10; n is an integer ranging from 5 to 15; and x is an integer ranging from 5 to 25. Commercially available silicone polyesters for use in the foaming formulations of the present disclosure are available from Siltech Corporation (Ontario, Canada).

Dicarboxylic acid compounds for use in the esterification reaction are commercially available from a variety of sources (e.g., BASF, Ludwigschafen, Germany) and conform to the following structure:

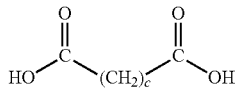

wherein c is an integer ranging from 1 to 10.

Suitably, $C_1$-$C_{10}$ saturated dicarboxylic acids for use in the esterification reaction are as follows:

| Common Name | c | Molecular Weight |
|---|---|---|
| Malonic | 1 | 104 |
| Succinic | 2 | 118 |
| Glutaric | 3 | 132 |
| Adipic | 4 | 146 |
| Pimelic | 5 | 160 |
| Subric | 6 | 174 |
| Azelaic | 7 | 188 |
| Sebacic | 8 | 202 |
| Undecanedioic | 9 | 216 |
| Dodecanedioic | 10 | 230 |

Poly(ethylene glycol) monomethyl ethers for use in the esterification reaction are commercially available from a variety of sources, such as FCI Technology (Gastonia, N.C.), and conform to the following structure:

wherein x is an integer from 5 to 25.

Suitable examples of poly(ethylene glycol) monomethyl ethers for use in the esterification reaction include the following:

| x | Molecular Weight |
|---|---|
| 5 | 237 |
| 8 | 367 |
| 15 | 676 |
| 23 | 1027 |
| 25 | 1116 |

LDMC compounds for use in the esterification reaction are commercially available from Siltech LLC (Lawrenceville, Ga.), and conform to the following structure:

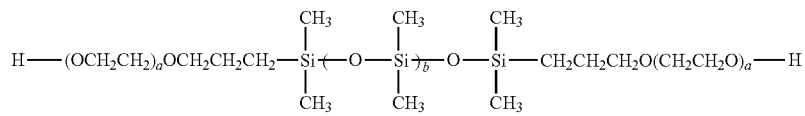

wherein a is an integer ranging from 5 to 20 and b is an integer ranging from 10 to 30.

Suitably, LDMC is selected from the following compounds:

| a | b | Molecular Weight |
|---|---|---|
| 5 | 10 | 1137 |
| 10 | 10 | 1357 |
| 20 | 10 | 1797 |
| 5 | 20 | 1876 |
| 10 | 20 | 2096 |
| 20 | 20 | 2536 |
| 5 | 30 | 2616 |
| 10 | 30 | 2836 |
| 20 | 30 | 3276 |

The values above were determined by $^{13}C$ NMR, $^{29}Si$ NMR and Gel Permeation Chromatography (GPC).

The foaming formulations include the silicone polyesters in amounts of from about 0.1% by weight to about 10% by weight, including from about 0.25% by weight to about 5% by weight, and including from about 0.5% by weight to about 4% by weight. In one suitable embodiment, the foaming formulation includes about 3.0% by weight silicone polyester.

In addition to the above, the foaming formulation may also include various optional agents to modify the physical, chemical, hedonic or processing characteristics of the formulations or serve as beneficial agents when used for a targeted purpose or in a targeted user population. The optional agents include, for example, emollients, humectants, moisturizers, botanicals, foam stabilizers, vitamins, disinfectants, non-aqueous solvents, preservatives, pH modifiers, sequestrants, antimicrobials, antioxidants, anti-reddening agents, astringents, deodorants, external analgesics, film formers, fragrances, hydrotropes, opacifiers, skin conditioning agents, skin exfoliating agents, skin protectants, sunscreens, thickeners, and the like.

Generally, emollients lubricate, soothe, and soften the skin surface. Exemplary emollients include oily or waxy ingredients such as esters, ethers, fatty alcohols, hydrocarbons, silicones, and the like, and combinations thereof. Particular emollients that may be used include ethoxylated and propoxylated alcohols, such as cetyl alcohols and ethoxylated lanolin.

Particular moisturizers could include, but are not to be limited to, PEG-7 glyceryl cocoate, isopropyl palmitate, $C_{12}$-$C_{15}$ alkyl benzoate, natural oils such as jojoba oil, synthetic oils such as mineral oil, silicones such as dimethicone, fatty alcohols and acids such as cetyl alcohol and stearic acid, waxes such as beeswax, and the like. One skilled in the art will recognize that this list is not all inclusive and could include any other suitable materials commonly known in the art or referenced in the Personal Care Products Council (PCPC) Compilation of Ingredients Used in Cosmetics in the United States (CIUCUS).

Humectants are hydroscopic agents that are widely used as moisturizers. Their function is to prevent the loss of moisture from the skin and to attract moisture from the environment. Common humectants include, for example, glycerin, propylene glycol, butylene glycol, betaine, sodium hyaluronate, sorbitol, urea, hydroxyethyl urea, and the like, and combinations thereof.

Exemplary disinfectants for use in the foaming formulations include triclosan, quaternary ammonium compounds, phenolics, and essential oils having antimicrobial action (e.g., thyme, eucalyptus, neem), and combinations thereof.

Another additive for use in the foaming formulation may be one or more non-aqueous solvents. Although not required, non-aqueous solvents may aid in dissolving certain components (e.g., preservatives, anti-microbial agent, etc.). Examples of some suitable non-aqueous solvents include, but are not limited to, glycerin, glycols, such as propylene glycol, butylene glycol, triethylene glycol, hexylene glycol, polyethylene glycols, ethoxydiglycol, and dipropyleneglycol; triglycerides, ethyl acetate, acetone, triacetin, and combinations thereof.

Preservatives for increasing the shelf life of the foaming formulations may also be used. Exemplary suitable preservatives include, but are not limited to, Kathon CG, which is a mixture of methylchloroisothiazolinone and methylisothiazolinone, available from Dow Chemical Company, Midland, Mich.; Mackstat H 66, available from Rhodia, member of the Solvay Group, Bristol, Pa.; DMDM hydantoin (e.g., Glydant Plus, Lonza, Inc., Switzerland); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Ashland Inc., Ashland, Ky., such as "Germall 115" (amidazolidinyl urea), "Germall II" (diazolidinyl urea), and "Germall Plus" (diazolidinyl urea and iodopropynyl butylcarbonate).

Suitable skin conditioning agents for use in the foaming formulations include quaternium and polyquaternium ingredients. Particularly suitable quaternium ingredients include behentrimonium chloride, behentrimonium methosulfate, cetrimonium chloride, cocotrimonium chloride, quaternium-79 hydrolyzed collagen, quaternium-80, quaternium-88, quaternium-95, and $C_{10}$-$C_{40}$ isoalkylamidopropylethyldimonium ethosulfate. Particularly suitable polyquaternium ingredients include polyquaternium-2, polyquaternium-7, polyquaternium-10, polyquaternium-68, polyquaterium-78, polyquaternium-82, and polymethylacrylamidopropyltrimonium chloride.

In general, the pH of the foaming formulations may be controlled to be within any desired range, depending on the targeted use. For bodily cleansing, it is typically desirable to have a foaming formulation with a neutral pH. If necessary, various pH modifiers may be utilized in the foaming formulation to achieve the desired pH level. For instance, some examples of basic pH modifiers that may be used in the formulations of the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the present disclosure include, but are not limited to, mineral acids; carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include carrageenic acid, humic acid, fulvic acid, and alginic acid.

In one embodiment, the foaming formulation may additionally include one or more sequestrants. A sequestrant is a substance whose molecules can form one or more bonds with a metal ion. In particular, water often contains metal ions, such as calcium ions, that might react with anionic components (e.g., acids) present within the foaming formulation. For example, in one embodiment, an anionic component that remains substantially unreacted with metal ions can better function as a cleansing agent. Some examples of sequestrants that may be used in the foaming formulations of the present disclosure include, but are not limited to, ethylenediamines, ethylenediaminetetraacetic acids (EDTA) acid and/or salts thereof, citric acids and/or salts thereof, glucuronic acids and/or salts thereof, iminodisuccinic acid and/or salts thereof, polyphosphates, organophosphates, dimercaprols, and the like.

In order to better enhance the antimicrobial efficacy of the foaming formulation, other optional antimicrobial agents (e.g., chlorhexidine digluconate, polyhexamethylene biguanide (PHMB), benzalkonium chloride, benzethonium chloride, cetyl pyridinium chloride) can be included in the formulation.

Still other optional agents include: antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); botanicals (e.g., Actiphyte of Aloe Vera 10 Fold GL, Actiphyte of Cucumber GL, Actiphyte of Japanese Green Tea GL, all from The Lubrizol Corporation, Wickliffe, Ohio); foam stabilizers (e.g. Polyox WSR 205 from Dow Chemical Company, Midland, Mich.); vitamins (e.g., tocopheryl acetate, retinyl palmitate, panthenol); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some antimicrobial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens and thickeners (to increase the viscosity of the formulation).

The amounts of the optional components will depend on the formulation to be prepared and the amounts of the other components in the foaming formulation.

In one particularly suitable embodiment, the foaming formulations of the present disclosure are substantially free of agents that are capable of forming micelles. In this context, and unless otherwise specified, the term "substantially free" means that the foaming formulations contain less than a functional amount of micelle-forming agents, typically less than 1.0%, including less than 0.50, including less than 0.1%, and also including zero percent, by weight of micelle-forming agents.

Micelle-forming agents, non-limiting examples of which include conventional ethoxylated silicones (e.g., Bis-PEG (10-20) dimethicones), 3-(3-hydroxypropyl)heptamethyltrisiloxane, polysiloxane betaine, and polyalkylene-modified siloxane block copolymers, used to create foam in conventional foaming formulations may cause the formulations to have poor aesthetics and/or skin feel properties such as a sticky, soapy, and/or tacky skin feel. Further, these conventional foaming formulations have poor foam stability (e.g., bubbly liquid having no overall order, no rigidity, etc.). Accordingly, by avoiding the use of these agents in the foaming formulation of the present disclosure, the foaming formulation provides improved cleansing and/or sanitizing to the skin of the user, and further has improved stability.

Methods of Preparing the Foaming Formulations

The foaming formulations are generally prepared by mixing all components together to form a homogeneous solution. Typically, the foaming formulation is prepared by mixing the water, alcohol, and silicone polyester (and, additionally, any further optional agents) together minimizing aeration. In one embodiment, the water, alcohol, and silicone polyester are mixed at room temperature.

Suitably, any solid components are first completely dissolved in water or other solvents before mixing with other components. The foaming formulation can be dispensed from a pump or aerosol as generally available in the art.

Methods of Use

The foaming formulations of the present disclosure can be used to provide effective cleansing and/or sanitizing of animate and inanimate surfaces. In one embodiment, the foaming formulations may be used to clean and/or sanitize a user's body. Particularly, in one suitable embodiment, the foaming formulations are in the form of liquid or gel formulations capable of being topically applied to the skin of a user to kill and/or inhibit the growth of bacteria and other microorganisms on the skin, particularly, on the hands, arms, and face of a user.

Moreover, the foaming formulations have improved stability such that the foaming formulations provide a cleansing effect for a sufficiently long period of time in order to effectively remove dirt and microorganisms. The foaming formulations have improved aesthetics (e.g., soft feel, improved foam appearance (e.g., even dispersion of foam from a dispensing device, smaller, more densely packed gas bubbles having uniform size and density, gas bubbles that do not degrade or convert quickly to a bubbly liquid)) and skin-feel.

Having described the disclosure in detail, it will be apparent that modifications and variations are possible without departing from the scope of the disclosure defined in the appended claims.

EXAMPLES

The following non-limiting Examples are provided to further illustrate the present disclosure.

Example 1

In this Example, a suitable foaming formulation of the present disclosure was prepared. The components of the formulation are shown in the table below.

| Component | INCI Name | Wt % |
|---|---|---|
| Water | | 24.02 |
| Silicone Polyester (Siltech Corporation, Ontario, Canada) | Methyl PEG-8 Bis-PEG-10 Dimethicone Succinate Copolymer | 3.00 |
| Polyox WSR 205 (Dow Chemical Company, Midland, Michigan) | PEG 14M | 0.08 |
| Ethyl Alcohol (Grain Processing Corporation, Muscatine, Iowa) | Ethyl Alcohol | 67.20 |
| Isopropyl Alcohol (Ashland, Inc., Ashland, Kentucky) | Isopropyl Alcohol | 5.05 |
| Betaine (Ashland, Inc., Ashland, Kentucky) | Betaine | 0.25 |
| Actiphyte of Aloe Vera 10 Fold GL (The Lubizol Corporation, Wickliffe, Ohio) | *Aloe Barbadensis* Leaf Extract; Water; Glycerin | 0.10 |
| Actiphyte of Cucumber GL (The Lubizol Corporation, Wickliffe, Ohio) | *Cucumis Sativus* (Cucumber) Fruit Extract; Water; Glycerin | 0.10 |
| Actiphyte of Japanese Green Tea GL (The Lubizol Corporation, Wickliffe, Ohio) | *Camellia Oleifera* Leaf Extract; Water; Glycerin | 0.10 |
| Vitamin B5 (DSM, The Netherlands) | Panthenol | 0.10 |
| Total | | 100.00 |

To prepare the formulation, water was first added to a vessel. While stirring the water, Polyox WSR 205 was slowly added and mixed until it was completely dissolved. The silicone polyester, plant extracts, betaine and panthenol were then added to the solution. Finally, ethanol and isopropyl alcohols were added, and the mixture was mixed to homogeneity at room temperature. The resulting formulation was clear in appearance.

Examples 2-11

In Examples 2-11, suitable foaming formulations of the present disclosure were prepared using the method described in Example 1. The components of the formulations are shown in the Table below.

| Component | INCI Name | Ex. 2 | Ex. 3 | Ex. 4 | Ex. 5 | Ex. 6 | Ex.7 | Ex. 8 | Ex. 9 | Ex. 10 | Ex. 11 |
|---|---|---|---|---|---|---|---|---|---|---|---|
| | | Wt % | | | | | | | | | |
| Water | | 24.17 | 23.87 | 23.67 | 23.67 | 23.87 | 24.47 | 24.37 | 24.37 | 24.67 | 24.67 |
| Silicone Polyester (Siltech Corporation, Ontario, Canada) | Methyl PEG-8 Bis-PEG-10 Dimethicone Succinate Copolymer | 3.00 | 3.00 | 3.00 | 3.00 | 3.00 | 3.00 | 3.00 | 3.00 | 3.00 | 3.00 |
| Polyox WSR 205 (Dow Chemical Company, Midland, Michigan) | PEG 14M | 0.08 | 0.08 | 0.08 | 0.08 | 0.08 | 0.08 | 0.08 | 0.08 | 0.08 | 0.08 |
| Ethyl Alcohol | Ethyl Alcohol | 67.20 | 67.20 | 67.20 | 67.20 | 67.20 | 67.20 | 67.20 | 67.20 | 67.20 | 67.20 |
| Isopropyl Alcohol | Isopropyl Alcohol | 5.05 | 5.05 | 5.05 | 5.05 | 5.05 | 5.05 | 5.05 | 5.05 | 5.05 | 5.05 |
| Glycerin | Glycerin | 0.50 | | | | | | | | | |
| Propylene glycol | Propylene glycol | | 0.80 | | | | | | | | |
| Betaine | Betaine | | | 1.00 | | | | | | | |
| Cetiol HE (BASF Care Chemicals, Itasca, Illinois) | PEG-7 Glyceryl Cocoate | | | | 1.00 | | | | | | |
| Tegosoft P (Evonik Industries AG, Germany) | Isopropyl Palmitate | | | | | 0.80 | | | | | |
| Finsolv TN (Innospec Active Chemicals, Newark, Delaware) | C12-C15 Alkyl Benzoate | | | | | | | 0.20 | | | |
| Actiphyte of Aloe Vera 10 Fold GL (The Lubrizol Corporation, Wickliffe, Ohio) | Aloe Barbadensis Leaf Extract; Water; Glycerin | | | | | | | | 0.10 | | |
| Actiphyte of Cucumber GL (The Lubrizol Corporation, Wickliffe, Ohio) | Cucumis Sativus (Cucumber) Fruit Extract; Water; Glycerin | | | | | | | | 0.10 | | |
| Actiphyte of Japanese Green Tea GL (The Lubrizol Corporation, Wickliffe, Ohio) | Camellia Oleifera Leaf Extract; Water; Glycerin | | | | | | | | 0.10 | | |
| Vitamin E Acetate | Tocopheryl Acetate | | | | | | | | 0.10 | | |
| Vitamin A Palmitate | Retinyl Palmitate | | | | | | | | 0.10 | | |
| Vitamin B5 | Panthenol | | | | | | | | 0.10 | | |
| Chlorhexidine Gluconate | Chlorhexidine Digluconate | | | | | | | | | 2.50 | |
| Fragrance | | | | | | | | | | | 0.10 |
| Total | | 100.00 | 100.00 | 100.00 | 100.00 | 100.00 | 100.00 | 100.00 | 100.00 | 100.00 | 100.00 |

Example 12

In this Example, formulations including silicone polyester as the foaming agent were evaluated for aesthetics and foam appearance.

Three formulations (Codes I, J, and K) were prepared using a silicone polyester, Methyl PEG-8 Bis-PEG-10 Dimethicone Succinate Copolymer (available from Siltech Corporation, Ontario, Canada), alone or with betaine, as shown in the table below. Further, a comparative foaming formulation including Silsurf Di-1010 (Bis-PEG-10 Dimethicone) (available from Siltech Corporation, Ontario, Canada) (Code M) was prepared.

| Code | I | J | K | M |
|---|---|---|---|---|
| Silicone Polyester | 3.00 | 3.00 | 3.00 | — |
| Betaine | — | 0.25 | 0.50 | 0.50 |
| Bis-PEG-10 Dimethicone | — | — | — | 2.6 |

Eight panelists evaluated the three test formulations (Codes I, J, K) for aesthetics/feel and foam appearance. Specifically, the panelists were to use the foaming formulation and rate them, based on aesthetics/feel and foam appearance (e.g., substantivity while in use, reduced stickiness/tackiness during and after use, soft and conditioned skin feel after formulation has dried, uniform size of foaming bubbles, compactness of foam, even flow rate of foam, etc.), from most preferred to least preferred. Then, the panelists were to compare their most preferred silicone polyester-containing formulation with the comparative foaming formulation of Code M. Again, the panelists were to use both their preferred silicone polyester-containing foaming formulation and the Code M comparative formulation and compare the formulations based on aesthetics/feel and foam appearance.

Prior to use of the foaming formulations, and in between uses of various formulations, the panelists were to thoroughly rub and rinse hands with warm water for 15 seconds. The formulation to be used was first consistently and slowly pumped from its dispenser for 5 pumps of foam into the sink prior to evaluation to ensure the mesh pump was warmed up. Then, to evaluate the formulation, 1-2 pumps of foam were slowly and consistently pumped into the panelist's hands. The panelists observed foam appearance in their hands. Further, as the formulation was spread around their hands, the panelists evaluated the aesthetics and feel of the formulation during use.

The results of the comparison between the silicone polyester-containing formulations and the comparative Code M formulation are shown in the table below.

| Code I v. Code M | | Code J v. Code M | | Code K v. Code M | |
|---|---|---|---|---|---|
| I | M | J | M | K | M |
| I | M | J | M | K | M |
| I | M | | | K | M |

*The code that received the greater acceptance is bolded and underlined.

As shown, the silicone polyester-containing formulations under Code J and Code K were both preferred over the Code M formulation 1000 of the time. More particularly, in the Code J and Code K formulations, in which betaine was included similarly to the betaine included in Code M, both Code J and Code K had superior aesthetics and skin feel as compared to Code M. Moreover, Code J was superior to Code M despite that Code J only includes half as much betaine. Further, even without betaine, the silicone polyester of Code I performed superior to Code M (including betaine) 33% of the time. Accordingly, this Example shows that the silicone polyester is more preferred as the foaming agent in a foaming formulation.

Example 13

In this Example, a foaming formulation according to the present disclosure was prepared and evaluated for its disinfecting ability against *E. coli*.

Specifically, the foaming formulation was evaluated using disinfectant suspension testing based on EN1500 (1997), available at http://wwww.cen.eu/cen/Products/EN/Pages/default.aspx. Initially, each of the left and right hands of 8 test subjects were swabbed and analyzed for the presence of *E. coli* (prevalue).

Each of the left and right hands of the 8 test subjects were then treated with 8 pumps of the foaming formulation. The formulation was then rubbed into the respective hand for a period of about 30 seconds. A second treatment of 8 pumps of the foaming formulation was then again applied to the left and right hands and the formulation was rubbed into the hands for a period of about 30 seconds.

The foaming formulation evaluated is set forth in the table below. The formulation was prepared as described in Example 1.

Test Foaming Formulation

| Trade Name | INCI Name | Approx. Wt % |
|---|---|---|
| Water | Water | 23.77 |
| Silicone Polyester (Siltech Corporation, Ontario, Canada) | Methyl PEG-8 Bis-PEG-10 Dimethicone Succinate Copolymer | 3.00 |
| Polyox WSR 205 (Dow Chemical Company, Midland, Michigan) | PEG 14M | 0.08 |
| Ethyl Alcohol (Grain Processing Corporation, Muscatine, Iowa) | Ethyl Alcohol | 67.20 |
| Isopropyl Alcohol (Ashland, Inc., Ashland, Kentucky) | Isopropyl Alcohol | 5.05 |
| Betaine (Ashland, Inc., Ashland, Kentucky) | Betaine | 0.50 |
| Actiphyte of Aloe Vera 10 Fold GL (The Lubrizol Corporation, Wickliffe, Ohio) | *Aloe Barbadensis* Leaf Extract; Water; Glycerin | 0.10 |
| Actiphyte of Cucumber GL (The Lubrizol Corporation, Wickliffe, Ohio) | *Cucumis Sativus* (Cucumber) Fruit Extract; Water; Glycerin | 0.10 |
| Actiphyte of Japanese Green Tea GL (The Lubrizol Corporation, Wickliffe, Ohio) | *Camellia Oleifera* Leaf Extract; Water; Glycerin | 0.10 |
| Vitamin B5 (DSM, The Netherlands) | Panthenol | 0.10 |
| Citric Acid | Citric Acid | q.s. |
| | Total | 100 |

The hands were then swabbed and analyzed for presence of *E. coli* (postvalue). The swabbed samples were diluted according to the method of EN1500. The disinfectant ability of the test foaming formulation was compared to the disinfectant ability of the EN1500 Reference formulation (70% isopropyl alcohol in water). The results are shown in the tables below.

|  | Hand (L/R) | Number of cfu per plate from dilution $10^x$ | | | | | | |
|---|---|---|---|---|---|---|---|---|
|  |  | Prevalue | | | Postvalue | | | |
|  |  | $10^{-3}$ | $10^{-4}$ | $10^{-5}$ | $10^{-0}$ | $10^{-1}$ | $10^{-2}$ | $10^{-3}$ |
| Test Formulation Sample 1 | L | >300 | >300 | 68 | >300 | 67 | <15 | <15 |
|  | R | >300 | >300 | 67 | >300 | 49 | <15 | <15 |
| Test Formulation Sample 2 | L | >300 | >300 | 74 | >300 | 20 | <15 | <15 |
|  | R | >300 | >300 | 65 | 233 | 30 | <15 | <15 |
| Test Formulation Sample 3 | L | >300 | >300 | 64 | >300 | 215 | <15 | <15 |
|  | R | >300 | >300 | 47 | >300 | 207 | 21 | <15 |
| Test Formulation Sample 4 | L | >300 | >300 | 38 | >300 | 160 | <15 | <15 |
|  | R | >300 | 285 | 22 | >300 | >300 | 41 | <15 |
| Test Formulation Sample 5 | L | 125 | <15 | <15 | >300 | 136 | <15 | <15 |
|  | R | 87 | <15 | <15 | >300 | 64 | <15 | <15 |
| Test Formulation Sample 6 | L | >300 | >300 | 59 | >300 | 92 | <15 | <15 |
|  | R | >300 | >300 | 53 | >300 | 83 | <15 | <15 |
| Test Formulation Sample 7 | L | >300 | >300 | 43 | >300 | 150 | <15 | <15 |
|  | R | >300 | 248 | 21 | >300 | 42 | <15 | <15 |
| Test Formulation Sample 8 | L | >300 | >300 | 51 | >300 | >300 | 36 | <15 |
|  | R | >300 | >300 | 54 | >300 | >300 | 51 | <15 |
| EN1500 Reference Formulation Sample 1 | L | >300 | >300 | 53 | >300 | 142 | <15 | <15 |
|  | R | >300 | >300 | 58 | >300 | 124 | <15 | <15 |
| EN1500 Reference Formulation Sample 2 | L | >300 | 258 | 31 | >300 | 141 | <15 | <15 |
|  | R | >300 | >300 | 44 | >300 | 157 | <15 | <15 |
| EN1500 Reference Formulation Sample 3 | L | >300 | >300 | 49 | >300 | 248 | 24 | <15 |
|  | R | >300 | >300 | 59 | >300 | >300 | 150 | <15 |
| EN1500 Reference Formulation Sample 4 | L | >300 | 257 | 26 | >300 | 44 | <15 | <15 |
|  | R | >300 | 285 | 31 | >300 | >300 | 26 | <15 |
| EN1500 Reference Formulation Sample 5 | L | 140 | <15 | <15 | >300 | 139 | 17 | <15 |
|  | R | 144 | <15 | <15 | >300 | 35 | <15 | <15 |
| EN1500 Reference Formulation Sample 6 | L | >300 | >300 | 63 | 55 | <15 | <15 | <15 |
|  | R | >300 | >300 | 93 | 235 | 20 | <15 | <15 |
| EN1500 Reference Formulation Sample 7 | L | >300 | >300 | 74 | >300 | 110 | 15 | <15 |
|  | R | >300 | >300 | 65 | 223 | 25 | <15 | <15 |

-continued

| | Hand | Prevalue | | | Postvalue | | |
|---|---|---|---|---|---|---|---|
| | (L/R) | $10^{-3}$ | $10^{-4}$ | $10^{-5}$ | $10^{-0}$ | $10^{-1}$ | $10^{-2}$ | $10^{-3}$ |

Number of cfu per plate from dilution $10^x$

| | Hand (L/R) | $10^{-3}$ | $10^{-4}$ | $10^{-5}$ | $10^{-0}$ | $10^{-1}$ | $10^{-2}$ | $10^{-3}$ |
|---|---|---|---|---|---|---|---|---|
| EN1500 Reference Formulation Sample 8 | L | >300 | >300 | 65 | >300 | 102 | <15 | <15 |
| | R | >300 | >300 | 81 | >300 | 287 | 30 | <15 |

| | Comparative Formulation | | | Test Formulation | | |
|---|---|---|---|---|---|---|
| Sample No. | Log pre-value | Log post-value | Log Reduction Factor | Log pre-value | Log post-value | Log Reduction Factor |
| 1 | 6.75 | 3.12 | 3.63 | 6.83 | 2.76 | 4.07 |
| 2 | 6.44 | 3.17 | 3.27 | 6.85 | 2.37 | 4.48 |
| 3 | 6.73 | 3.55 | 3.18 | 6.75 | 3.32 | 3.43 |
| 4 | 6.43 | 2.80 | 3.63 | 6.46 | 3.26 | 3.20 |
| 5 | 5.15 | 2.96 | 2.19 | 5.03 | 3.00 | 2.03 |
| 6 | 6.89 | 2.17 | 4.72 | 6.75 | 2.94 | 3.81 |
| 7 | 6.85 | 2.49 | 4.36 | 6.41 | 2.98 | 3.43 |
| 8 | 6.86 | 3.30 | 3.56 | 6.72 | 3.64 | 3.08 |
| Mean | 6.51 | 2.95 | 3.57 | 6.48 | 3.03 | 3.44 |
| Standard Deviation | 0.58 | 0.45 | 0.77 | 0.61 | 0.38 | 0.74 |

As shown in the tables, the test foaming formulation including the silicone polyester as the foaming agent was capable of disinfecting the hands of the test subjects as well as the EN1500 Reference foaming formulation.

Example 14

In this Example, a foaming formulation according to the present disclosure was prepared and evaluated for its disinfecting ability against *E. coli*.

Specifically, the foaming formulation was evaluated using disinfectant suspension testing based on EN1500 (1997) as described in Example 13. The disinfectant ability of the test foaming formulation was compared to the disinfectant ability of the EN1500 Reference formulation (70% isopropyl alcohol in water).

The foaming formulation evaluated is set forth in the table below. The formulation was prepared as described in Example 1.

Test Foaming Formulation

| Trade Name | INCI Name | Approx. Wt % |
|---|---|---|
| Water | Water | 21.25 |
| Silicone Polyester (Siltech Corporation, Ontario, Canada) | Methyl PEG-8 Bis-PEG-10 Dimethicone Succinate Copolymer | 3.00 |
| Polyox WSR 205 (Dow Chemical Company, Midland, Michigan) | PEG 14M | 0.10 |
| Ethyl Alcohol (Grain Processing Corporation, Muscatine, Iowa) | Ethyl Alcohol | 67.20 |
| Isopropyl Alcohol (Ashland, Inc., Ashland, Kentucky) | Isopropyl Alcohol | 5.05 |
| Chlorohexidine Gluconate | Digluconate | 2.50 |
| Betaine (Ashland, Inc., Ashland, Kentucky) | Betaine | 0.50 |
| Actiphyte of Aloe Vera 10 Fold GL (The Lubrizol Corporation, Wickliffe, Ohio) | *Aloe Barbadensis* Leaf Extract; Water; Glycerin | 0.10 |
| Actiphyte of Cucumber GL (The Lubrizol Corporation, Wickliffe, Ohio) | *Cucumis Sativus* (Cucumber) Fruit Extract; Water; Glycerin | 0.10 |
| Actiphyte of Japanese Green Tea GL (The Lubrizol Corporation, Wickliffe, Ohio) | *Camellia Oleifera* Leaf Extract; Water; Glycerin | 0.10 |
| Vitamin B5 (DSM, The Netherlands) | Panthenol | 0.10 |
| Purac FF88 (Purac, Lincolnshire, Illinois) | Lactic Acid | q.s. |
| | Total | 100.00 |

The results are shown in the tables below.

Number of cfu per plate from dilution $10^x$

| | Hand (L/R) | $10^{-3}$ | $10^{-4}$ | $10^{-5}$ | $10^{-0}$ | $10^{-1}$ | $10^{-2}$ | $10^{-3}$ |
|---|---|---|---|---|---|---|---|---|
| Test Formulation Sample 1 | L | >300 | >300 | 39 | >300 | 66 | <15 | <15 |
| | R | >300 | 242 | 30 | >300 | 58 | <15 | <15 |

-continued

| | | Number of cfu per plate from dilution $10^x$ | | | | | | |
|---|---|---|---|---|---|---|---|---|
| | Hand | Prevalue | | | | Postvalue | | |
| | (L/R) | $10^{-3}$ | $10^{-4}$ | $10^{-5}$ | $10^{-0}$ | $10^{-1}$ | $10^{-2}$ | $10^{-3}$ |
| Test Formulation Sample 2 | L | 67 | <15 | <15 | 134 | 16 | <15 | <15 |
| | R | 176 | 25 | <15 | 26 | <15 | <15 | <15 |
| Test Formulation Sample 3 | L | >300 | >300 | 48 | 264 | 29 | <15 | <15 |
| | R | >300 | >300 | 69 | >300 | 37 | <15 | <15 |
| Test Formulation Sample 4 | L | >300 | >300 | 40 | >300 | 95 | <15 | <15 |
| | R | >300 | >300 | 100 | >300 | 209 | 16 | <15 |
| Test Formulation Sample 5 | L | 125 | >300 | 44 | >300 | >300 | 55 | <15 |
| | R | 87 | >300 | 52 | >300 | 71 | <15 | <15 |
| Test Formulation Sample 6 | L | >300 | 127 | 19 | >300 | >300 | 99 | <15 |
| | R | >300 | >301360 | 22 | >300 | >300 | 41 | <15 |
| Test Formulation Sample 7 | L | >300 | >300 | 82 | 239 | 24 | <15 | <15 |
| | R | >300 | >300 | 99 | >300 | 66 | <15 | <15 |
| Test Formulation Sample 8 | L | >300 | >300 | 151 | 148 | 15 | <15 | <15 |
| | R | >300 | >300 | 98 | >300 | 46 | <15 | <15 |
| EN1500 Reference Formulation Sample 1 | L | N/A | 239 | 31 | >300 | 41 | <15 | <15 |
| | R | N/A | 111 | 16 | >300 | 51 | <15 | <15 |
| EN1500 Reference Formulation Sample 2 | L | N/A | 103 | <15 | 47 | <15 | <15 | <15 |
| | R | N/A | 132 | 16 | 23 | <15 | <15 | <15 |
| EN1500 Reference Formulation Sample 3 | L | N/A | 280 | 25 | 256 | 37 | <15 | <15 |
| | R | N/A | 136 | 17 | 223 | 18 | <15 | <15 |
| EN1500 Reference Formulation Sample 4 | L | N/A | >300 | 68 | >300 | 27 | <15 | <15 |
| | R | N/A | >300 | 73 | >300 | 68 | <15 | <15 |
| EN1500 Reference Formulation Sample 5 | L | N/A | >300 | 62 | >300 | >300 | 50 | <15 |
| | R | N/A | >300 | 77 | >300 | 131 | 17 | <15 |
| EN1500 Reference Formulation Sample 6 | L | N/A | >300 | 126 | >300 | >300 | 44 | <15 |
| | R | N/A | >300 | 63 | >300 | 217 | 27 | <15 |
| EN1500 Reference Formulation Sample 7 | L | N/A | >300 | 80 | 4 | <15 | <15 | <15 |
| | R | N/A | >300 | 69 | 97 | <15 | <15 | <15 |
| EN1500 Reference Formulation Sample 8 | L | N/A | >300 | 139 | >300 | 63 | <15 | <15 |
| | R | N/A | >300 | 112 | 240 | 41 | <15 | <15 |

N/A denotes that the dilution was not performed as actual value already determined.

| Sample No. | Comparative Formulation | | | Test Formulation | | |
|---|---|---|---|---|---|---|
| | Log pre-value | Log post-value | Log Reduction Factor | Log pre-value | Log post-value | Log Reduction Factor |
| 1 | 6.26 | 2.66 | 3.60 | 6.41 | 2.79 | 3.62 |
| 2 | 6.08 | 1.54 | 4.54 | 5.11 | 1.92 | 3.19 |
| 3 | 6.32 | 2.39 | 3.93 | 6.77 | 2.44 | 4.33 |
| 4 | 6.85 | 2.68 | 4.17 | 6.85 | 3.18 | 3.67 |
| 5 | 6.85 | 3.22 | 3.63 | 6.68 | 3.06 | 3.62 |
| 6 | 6.98 | 3.38 | 3.60 | 6.14 | 3.85 | 2.29 |
| 7 | 6.88 | 1.71 | 5.17 | 6.96 | 2.44 | 4.52 |
| 8 | 7.10 | 2.46 | 4.64 | 7.10 | 2.24 | 4.86 |
| Mean | 6.67 | 2.51 | 4.16 | 6.50 | 2.74 | 3.76 |
| Standard Deviation | 0.38 | 0.64 | 0.58 | 0.64 | 0.61 | 0.81 |

As shown in the tables, the test foaming formulation including the silicone polyester as the foaming agent was capable of disinfecting the hands of the test subjects as well as, or superior to, the EN1500 Reference foaming formulation.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above formulations without departing from the scope of the disclosure, it is intended that all matter contained in the above description shall be interpreted as illustrative and not in a limiting sense.

What is claimed is:

1. A foaming formulation comprising water, an alcohol, and a silicone polyester, wherein the silicone polyester comprises the following structure:

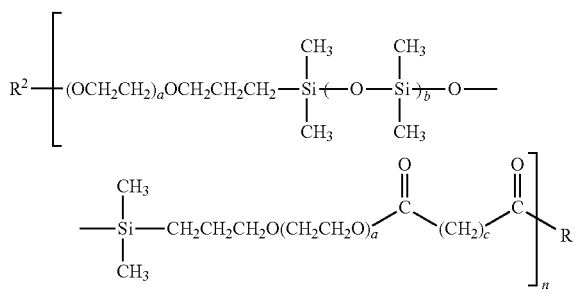

wherein $R^1$ is $-O(CH_2CH_2O)_xCH_3$; $R^2$ is $-C(O)(CH_2)_cC(O)O(CH_2CH_2O)_xCH_3$; a is an integer ranging from 5 to 20; b is an integer ranging from 10 to 30; c is an integer ranging from 1 to 10; n is an integer ranging from 5 to 15; and x is an integer ranging from 5 to 25.

2. The foaming formulation of claim 1 comprising from about 5.0% by weight to about 45% by weight water, from 50% by weight to about 90% by weight alcohol, and from about 0.1% by weight to about 10% by weight silicone polyester.

3. The foaming formulation of claim 1 comprising from about 10% by weight to about 40% by weight water.

4. The foaming formulation of claim 1 comprising from about 20% by weight to about 30% by weight water.

5. The foaming formulation of claim 1, wherein the alcohol is selected from the group consisting of methanol, ethanol, n-propanol, isopropanol, n-butanol, tert-butanol, 2-butanol, pentanol, hexanol, and combinations thereof.

6. The foaming formulation of claim 1 comprising from about 60% by weight to about 80% by weight alcohol.

7. The foaming formulation of claim 1 comprising from about 65% by weight to about 75% by weight alcohol.

8. The foaming formulation of claim 1 comprising from about 0.25% by weight to about 5% by weight silicone polyester.

9. The foaming formulation of claim 1 comprising from about 0.5% by weight to about 4% by weight silicone polyester.

10. The foaming formulation of claim 1 further comprising at least one agent selected from the group consisting of emollients, humectants, moisturizers, botanicals, foam stabilizers, vitamins, disinfectants, non-aqueous solvents, preservatives, pH modifiers, sequestrants, antimicrobials, antioxidants, anti-reddening agents, astringents, deodorants, external analgesics, film formers, fragrances, hydrotropes, opacifiers, skin conditioning agents, skin exfoliating agents, skin protectants, sunscreens, and thickeners.

11. A process of preparing a foaming formulation, the process comprising mixing water, an alcohol, and a silicone polyester, wherein the silicone polyester comprises the following structure:

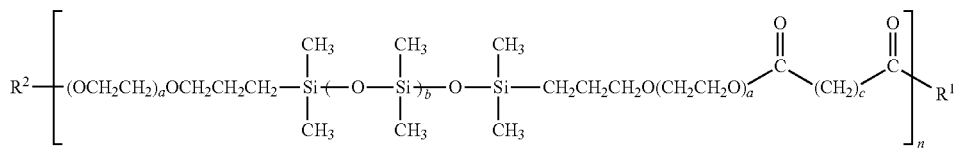

wherein $R^1$ is $-O(CH_2CH_2O)_xCH_3$; $R^2$ is $-C(O)(CH_2)_cC(O)O(CH_2CH_2O)_xCH_3$; a is an integer ranging from 5 to 20; b is an integer ranging from 10 to 30; c is an integer ranging from 1 to 10; n is an integer ranging from 5 to 15; and x is an integer ranging from 5 to 25.

12. The process of claim 11, wherein from about 5% by weight to about 45% by weight of water, from 50% by weight to about 90% by weight of the alcohol, and from about 0.1% by weight to about 10% by weight of the silicone polyester are mixed.

13. The process of claim 11, wherein from about 10% by weight to about 40% by weight of water, from about 60% by weight to about 80% by weight of the alcohol, and from about 0.25% by weight to about 5% by weight of the silicone polyester are mixed.

14. The process of claim 11, wherein from about 20% by weight to about 30% by weight of water, from about 65% by weight to about 75% by weight of the alcohol, and from about 0.5% by weight to about 4% by weight of the silicone polyester are mixed.

15. The process of claim 11, wherein the alcohol is selected from the group consisting of methanol, ethanol, n-propanol, isopropanol, n-butanol, tert-butanol, 2-butanol, pentanol, hexanol, and combinations thereof.

16. A method for bodily cleansing comprising topically applying to skin a foaming formulation comprising water, an alcohol, and a silicone polyester, wherein the silicone polyester comprises the following structure:

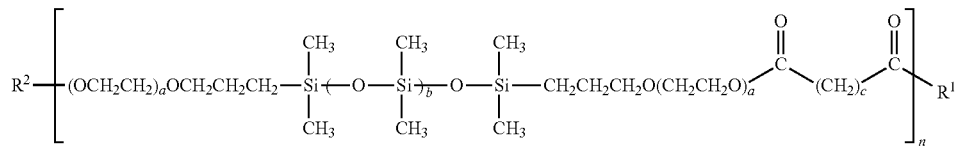

wherein R¹ is —O(CH₂CH₂O)$_x$CH₃; R² is —C(O)(CH₂)$_c$C(O)O(CH₂CH₂O)$_x$CH₃; a is an integer ranging from 5 to 20; b is an integer ranging from 10 to 30; c is an integer ranging from 1 to 10; n is an integer ranging from 5 to 15; and x is an integer ranging from 5 to 25.

17. The method of claim 16, wherein the foaming formulation comprises from about 5.0% by weight to about 45% by weight water, from 50% by weight to about 90% by weight alcohol, and from about 0.1% by weight to about 10% by weight silicone polyester.

18. The method of claim 16, wherein the alcohol is selected from the group consisting of methanol, ethanol, n-propanol, isopropanol, n-butanol, tert-butanol, 2-butanol, pentanol, hexanol, and combinations thereof.

19. The method of claim 16, wherein the foaming formulation comprises from about 0.25% by weight to about 5% by weight silicone polyester.

20. The method of claim 16, wherein the foaming formulation comprises from about 0.5% by weight to about 4% by weight silicone polyester.

* * * * *